United States Patent
Steinbuss

(10) Patent No.: US 8,081,768 B2
(45) Date of Patent: Dec. 20, 2011

(54) METHOD AND APPARATUS FOR DETERMINING A TARGET AMPLIFICATION CURVE FOR A HEARING DEVICE

(75) Inventor: Andre Steinbuss, Nürnberg (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1265 days.

(21) Appl. No.: 11/799,957

(22) Filed: May 3, 2007

(65) Prior Publication Data

US 2007/0258609 A1 Nov. 8, 2007

(30) Foreign Application Priority Data

May 4, 2006 (DE) .......................... 10 2006 020 833

(51) Int. Cl.
*H04R 29/00* (2006.01)
*H04R 25/00* (2006.01)
(52) U.S. Cl. ............................. 381/60; 381/312; 381/320
(58) Field of Classification Search .................. 381/60, 381/312–331; 600/559; 73/585
See application file for complete search history.

(56) References Cited

U.S. PATENT DOCUMENTS

| 4,953,112 A | 8/1990 | Widin et al. |
| 6,496,585 B1 * | 12/2002 | Margolis .......................... 381/60 |
| 7,704,216 B2 * | 4/2010 | Margolis ........................ 600/559 |

FOREIGN PATENT DOCUMENTS

EP 0396 831 B1 11/1990

OTHER PUBLICATIONS

O'Neill et al., Systematic errors in bone conduction audiometry, 2000, Clin. Otolaryngol. 25, 468-470.*

* cited by examiner

*Primary Examiner* — Davetta W Goins
*Assistant Examiner* — Matthew Eason

(57) ABSTRACT

To determine target amplification curves in hearing devices, audiometric mismeasurements are to be corrected. To this end, it is proposed first to measure a bone conduction hearing threshold of a patient. Furthermore a database having typical sound conduction components for a number of typical hearing impairments is provided. One of these sound conduction components is selected in order to smooth the measured bone conduction hearing threshold, with a smoothed bone conduction hearing threshold resulting. One or a number of target amplification curves is formed from the smoothed bone conduction hearing threshold, if necessary with further hearing thresholds. Error corrections can be reliably carried out with the aid of the database.

18 Claims, 1 Drawing Sheet

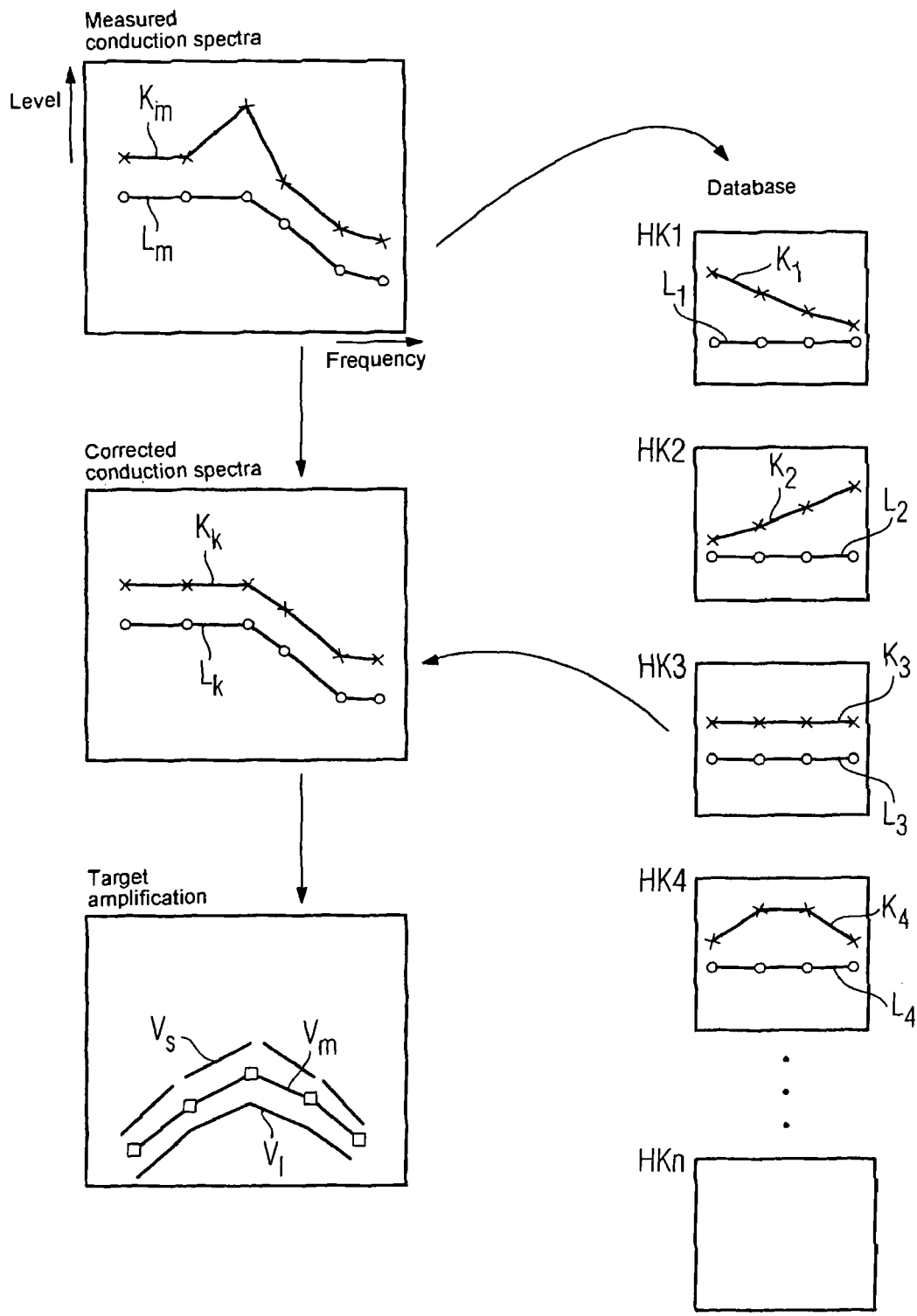

METHOD AND APPARATUS FOR DETERMINING A TARGET AMPLIFICATION CURVE FOR A HEARING DEVICE

CROSS REFERENCE TO RELATED APPLICATIONS

This application claims priority of German application No. 10 2006 020 833.1 filed May 4, 2006, which is incorporated by reference herein in its entirety.

FIELD OF THE INVENTION

The present invention relates to a method for determining a target amplification curve for a hearing device by measuring a bone conduction hearing threshold of a patient. Furthermore, the present invention relates to a corresponding apparatus for determining a target amplification curve.

BACKGROUND OF THE INVENTION

Pure-tone audiometric data generally forms the basis for hearing device adjustment, said data being captured by the responsible audiologist or hearing device acoustician in the form of a pure-tone audiogram. This data establishes the basis for the calculation of target amplification curves to compensate for the existing hearing loss.

Bone conduction and air conduction hearing thresholds as well as the discomfort threshold are generally captured by pure-tone audiometry. To satisfy the changing requirements to compensate for sound conduction hearing impairments or combined hearing impairments, sound conduction components, i.e. the difference between the air conduction hearing threshold and the bone conduction hearing threshold, are weighted to a significantly greater degree and contribute massively to a changed target amplification curve, as a function of the adjustment strategy selected. Possible mismeasurements or incomplete measurements of bone conduction can thus massively influence the resulting target amplification curves and have a significant negative influence on the spontaneous acceptance of a hearing system.

Furthermore the measurement of the bone conduction is significantly prone to error by virtue of its nature. In the low frequency range, feeling thresholds influence the measurement result and in the high frequency range the result of the measurement depends significantly on the individual position of the bone conduction receiver. The measurement results of a bone conduction measurement are thus of little value and possible errors have a massive influence on the calculation of the target amplification curve.

Patent application EP 0396 831 B1 discloses a method and an apparatus for determining acoustic parameters in a hearing device. In this context the target hearing sensitivity of the user and the transmission function of the hearing device are first determined. A software model of the transmission function is subsequently stored and the acoustic parameters of the hearing device are optimized by comparing the hearing sensitivity of the software model with the target hearing sensitivity and by setting the acoustic parameters, in order to minimize comparison errors.

In practice, errors established in the hearing device setting are manually corrected. If this is not possible in a quick and easy manner, the user often selects another hearing system.

SUMMARY OF THE INVENTION

The object of the present invention thus consists in reliably determining a target amplification curve for a hearing device and correcting measurement errors where applicable.

In accordance with the invention, this object is achieved by a method for determining a target amplification curve for a hearing device by measuring a bone conduction hearing threshold of a patient, providing a database with typical sound conduction components for several typical hearing impairments, selecting a sound conduction component from the database, smoothing the measured bone conduction hearing threshold on the basis of the selected sound conduction component and determining the target amplification curve as a function of the smoothed bone conduction hearing threshold. In this context, typical sound conduction components signify the difference between the air conduction hearing threshold and the bone conduction hearing threshold for typical hearing losses. The sound conduction components characterize the middle ear hearing impairment.

Furthermore, an apparatus is provided in accordance with the invention for determining a target amplification curve for a hearing device having a measuring facility for measuring a bone conduction hearing threshold of a patient, a storage facility for storing a database with typical sound conduction components for a number of typical hearing impairments and a computing facility for automatically selecting a typical sound conduction component from the database, to smooth the measured bone conduction hearing threshold on the basis of the selected sound conduction component and to determine the target amplification curve as a function of the smoothed bone conduction hearing threshold.

Error-free target amplification curves can be determined, prior to the calculation of the target amplification curves, by means of the correction of bone conduction data according to the invention, this being reflected in the spontaneous acceptance of the hearing system, particularly for combined hearing losses after the initial adjustment. For the adjusting audiologist and respectively hearing device acoustician, this signifies less time expenditure for a subsequent adjustment and respectively exoneration from the need for a further adjustment attempt Pursuant to an embodiment according to the invention, that sound conduction component can be selected from the database, which correlates best with the measured sound conduction component at least in a predetermined spectrum segment. Incorrect measuring points can be easily identified and corrected in this way.

The method according to the invention can advantageously be used to determine a first target amplification curve for a first volume category and also to determine at least one further target amplification curve for at least one further volume category for the hearing device. The typical target amplification curves can thus be reliably determined for quiet, medium and loud levels.

BRIEF DESCRIPTION OF THE DRAWINGS

The present invention is now described in more detail with reference to the appended drawing, which shows a flow chart of the method according to the invention.

DETAILED DESCRIPTION OF THE INVENTION

The exemplary embodiment described in more detail below represents a preferred embodiment of the present invention.

To determine a correct target amplification and/or a correct family of target amplification curves, the pure-tone audiometric data is generally initially measured in the form of a bone conduction and an air conduction hearing threshold. Both hearing thresholds spectrally reproduce the volume level which can still be perceived. The top left of the FIGURE shows the measured air conduction hearing threshold $L_m$ and the measured bone conduction hearing threshold $K_m$. Both hearing thresholds run essentially parallel to one another. The bone conduction hearing threshold $K_m$ only differs at one point, which suggests a mismeasurement. To reduce the frequency of mismeasurements, a prior examination and correction of the bone conduction values are thus carried out in accordance with the invention.

To smooth or correct the bone conduction hearing threshold in accordance with the invention, advantage is taken of the knowledge that the number of pathological changes to the middle ear leading to a sound conduction hearing impairment, which is reflected in the bone conduction, is transparent. Furthermore, the influence of the middle ear changes on the bone conduction hearing threshold is known as far as possible in each instance in terms of type, degree and pattern. An assignment to a known clinical picture having a typical pattern of the bone conduction threshold or a combination of two or more causes can thus be carried out on the basis of the existing bone conduction values. After said assignment, the outliers of the bone conduction measurement can be corrected and the target amplification curves can be calculated using the modified data.

In the concrete example in the FIGURE, a database having bone conduction and air conduction hearing thresholds and respectively sound conduction components for a number of hearing loss categories, each representing a specific pathological clinical picture, was recorded with its typical spectral patterns. By way of example, in the case of a first hearing loss category HK1, the bone conduction hearing threshold $K_1$ and the air conduction hearing threshold $L_1$ approximate to one another in the high frequency range. In the case of a second symbolic hearing loss category HK2, the two hearing thresholds $K_2$ and $L_2$ diverge in the high frequency range. In the case of the hearing loss category HK3, the two hearing thresholds $K_3$ and $L_3$ run parallel to one another. In the case of another hearing loss category HK4, the two hearing thresholds $K_4$ and $L_4$ are further apart from one another in a medium frequency range and are close together in the high and respectively low frequency range. The database can include numerous further hearing loss categories HKn. In the present case, the spectra of the different categories are characterized in that they exhibit a specific distance pattern in relation to one another.

The measured conduction spectra $K_m$ and $L_m$ here run essentially parallel to one another with the exception of one measuring point. A comparison with the database shows that the bone conduction hearing threshold $K_3$ runs parallel to the air conduction hearing threshold $L_3$ in the hearing loss category HK3. The measured hearing thresholds can thus be assigned with high probability to the hearing loss category HK3. The significantly differing measuring point in the measured bone conduction spectrum is thus in all likelihood a mismeasurement. The measured bone conduction hearing threshold $K_m$ is thus corrected with the aid of the hearing thresholds $K_3$, $L_3$ of the hearing loss category HK3, so that a corrected bone conduction hearing threshold $K_k$ results. This corrected bone conduction hearing threshold is shown in the center on the left in the FIGURE. The associated air conduction hearing threshold $L_k$ can remain unchanged and can correspond to the measured air conduction hearing threshold $L_m$ or can also be corrected where necessary.

The target amplification curves $V_s$ for quiet levels, $V_m$ for average levels and $V_t$ for loud levels are created from the corrected conduction hearing thresholds $K_k$ and $L_k$. A hearing device adjustment using target amplification curves is thus possible, said target amplification curves being based on corrected audiometric data.

With the above-mentioned example only spectra for the bone conduction hearing threshold and the air conduction hearing threshold and/or their differences, the sound conduction components, were recorded in the database for each hearing loss category. Alternatively a database could also be established just with bone conduction hearing thresholds and correction could take place only on the basis of the typical bone conduction hearing threshold patterns. A further alternative consists in the discomfort threshold or another threshold being recorded in addition to the bone conduction hearing threshold or the two hearing thresholds for each hearing loss category. In some circumstances this allows an improved assignment between the measurement curves and the hearing loss categories to be achieved, so that a more reliable correction of mismeasurements can take place.

The invention claimed is:

1. A method for determining a target amplification curve for a hearing device to be worn by a patient, comprising:
   measuring a bone conduction hearing threshold of the patient by a measurement unit;
   providing a database having a plurality of typical sound conduction components for a plurality of typical hearing impairments by a storage unit;
   selecting a sound conduction component from the database by a computing unit;
   smoothing the measured bone conduction hearing threshold based on the selected sound conduction component by the computing unit; and
   determining the target amplification curve as a function of the smoothed bone conduction hearing threshold by the computing unit.

2. The method as claimed in claim 1, wherein the selected sound conduction component comprises a typical bone conduction hearing threshold.

3. The method as claimed in claim 1, wherein the selected sound conduction component correlates with the measured bone conduction hearing threshold at least in a predetermined spectrum segment.

4. The method as claimed in claim 1, wherein an air conduction hearing threshold is measured together with the bone conduction hearing threshold.

5. The method as claimed in claim 4, wherein the selected sound conduction component comprises a pair of typical bone conduction hearing threshold and air conduction hearing threshold.

6. The method as claimed in claim 5, wherein the selected pair of air conduction hearing threshold and bone conduction hearing threshold correlates with the measured pair of air conduction hearing threshold and bone conduction hearing threshold at least in a predetermined spectral segment.

7. The method as claimed in claim 5, wherein a distance pattern between the selected pair of typical bone conduction hearing threshold and air conduction hearing threshold correlates with a distance pattern between the measured pair of bone conduction hearing threshold and air conduction hearing threshold at least in a predetermined spectral segment.

8. The method as claimed in claim 1, wherein the target amplification curve is determined for a volume category.

9. The method as claimed in claim 1, wherein a plurality of target amplification curves are determined for a plurality of different volume categories.

10. A device for determining a target amplification curve for a hearing device to be worn by a patient, comprising:

a measurement unit that measures a bone conduction hearing threshold of the patient;

a storage unit that stores a database comprising a plurality of typical sound conduction components for a plurality of typical hearing impairments; and a computing unit that:
automatically selects a sound conduction component from the database,
smoothes the measured bone conduction hearing threshold based on the selected sound conduction component, and
determines the target amplification curve as a function of the smoothed bone conduction hearing threshold.

11. The device as claimed in claim 10, wherein the selected sound conduction component comprises a typical bone conduction hearing threshold.

12. The device as claimed in claim 10, wherein the selected sound conduction component correlates with the measured bone conduction hearing threshold at least in a predetermined spectrum segment.

13. The device as claimed in claim 10, wherein an air conduction hearing threshold is measured together with the bone conduction hearing threshold.

14. The device as claimed in claim 13, wherein the selected sound conduction component comprises a pair of typical bone conduction hearing threshold and air conduction hearing threshold.

15. The device as claimed in claim 14, wherein the selected pair of air conduction hearing threshold and bone conduction hearing threshold correlates with the measured pair of air conduction hearing threshold and bone conduction hearing threshold at least in a predetermined spectral segment.

16. The device as claimed in claim 14, wherein a distance pattern between the selected pair of typical bone conduction hearing threshold and air conduction hearing threshold correlates with a distance pattern between the measured pair of bone conduction hearing threshold and air conduction hearing threshold at least in a predetermined spectral segment.

17. The device as claimed in claim 10, wherein the target amplification curve is determined for a volume category.

18. The device as claimed in claim 10, wherein a plurality of target amplification curves are determined for a plurality of different volume categories.

* * * * *